United States Patent [19]

Ackermann et al.

[11] 4,348,408
[45] Sep. 7, 1982

[54] PESTICIDAL α-ALLENYL-3-PHENOXYBENZYL-2,2-DIMETHYL-3-(2,2-DIHALOVINYL)-CYCLOPROPANE-1-CARBOXYLATES

[75] Inventors: Peter Ackermann, Reinach; Laurenz Gsell, Basel; Rudolf Wehrli, Rheinfelden, all of Switzerland

[73] Assignee: Ciba-Geigy Corporation, Ardsley, N.Y.

[21] Appl. No.: 292,080

[22] Filed: Aug. 12, 1981

[30] Foreign Application Priority Data

Aug. 22, 1980 [CH] Switzerland ............ 6353/80
Jun. 30, 1981 [CH] Switzerland ............ 4304/81

[51] Int. Cl.³ .................. C07C 69/743; A01N 53/00
[52] U.S. Cl. ................... 424/305; 560/124; 568/637; 568/638; 568/639
[58] Field of Search ................ 560/124; 424/305

[56] References Cited

U.S. PATENT DOCUMENTS

| | | | |
|---|---|---|---|
| 3,973,036 | 8/1976 | Hirano | 560/124 |
| 4,024,163 | 5/1977 | Elliott | 560/124 |
| 4,199,596 | 4/1980 | Fuchs | 560/124 |
| 4,219,564 | 8/1980 | Drabek | 560/124 |

FOREIGN PATENT DOCUMENTS 10727 5/1980 European Pat. Off. ............ 560/124

Primary Examiner—Michael L. Shippen
Attorney, Agent, or Firm—Frederick H. Rabin

[57] ABSTRACT

The invention describes cyclopropanecarboxylic acid α-allenyl-3-phenoxybenzyl esters of the formula

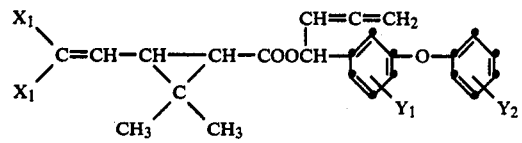

wherein $X_1$ is halogen and each of $Y_1$ and $Y_2$ is hydrogen or halogen, a process for the production of these compounds, and the use thereof for controlling a variety of pests of animals and plants. The intermediates of the formula

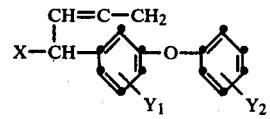

wherein X is hydroxyl or halogen and each of $Y_1$ and $Y_2$ is hydrogen or halogen, are also described.

12 Claims, No Drawings

PESTICIDAL α-ALLENYL-3-PHENOXYBENZYL-2,2-DIMETHYL-3-(2,2-DIHALOVINYL)-CYCLOPROPANE-1-CARBOXYLATES

The present invention relates to cyclopropanecarboxylic acid α-allenyl-3-phenoxybenzyl esters, to the production thereof, and to the use thereof in pest control. The cyclopropanecarboxylic acid α-allenyl-3-phenoxybenzyl esters have the formula

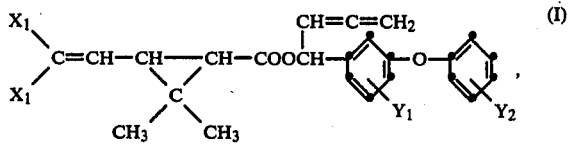

wherein $X_1$ is halogen and each of $Y_1$ and $Y_2$ is hydrogen or halogen.

Halogen in the above definition denotes fluorine, chlorine, bromine or iodine, with fluorine, chlorine or bromine being preferred.

Preferred compounds are those of the formula I, wherein $X_1$ is fluorine or chlorine, $Y_1$ is hydrogen and $Y_2$ is hydrogen, fluorine, chlorine or bromine.

The most preferred compounds are those of the formula I, wherein $X_1$ is chlorine, $Y_1$ is hydrogen and $Y_2$ is hydrogen, fluorine or chlorine.

The compounds of the formula I are obtained by methods which are known per se, e.g. as follows:

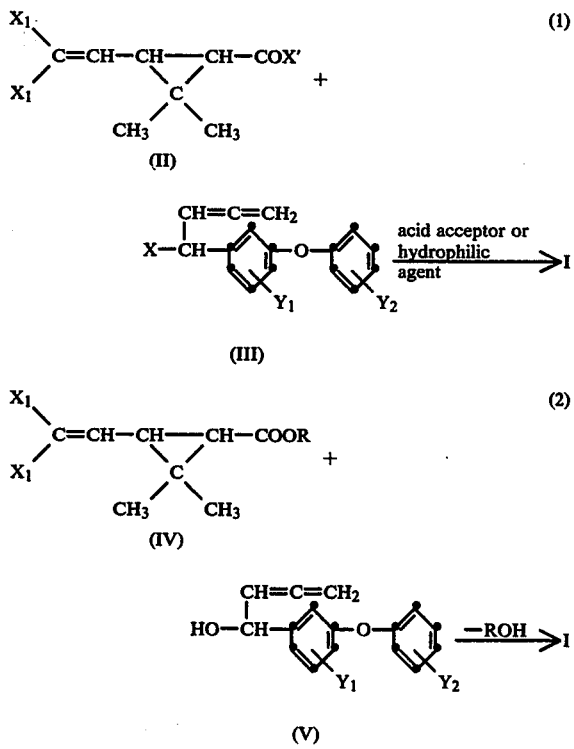

In formulae II to V above, $X_1$, $Y_1$ and $Y_2$ are as defined for formula I.

In formulae II and III, one of X and X' is a hydroxyl group and the other is a halogen atom, especially chlorine or bromine, and R in formula IV is $C_1$–$C_4$ alkyl, preferably methyl or ethyl.

Suitable acid acceptors are in particular tertiary amines, such as trialkylamines and pyridine, and also hydroxides, oxides, carbonates and bicarbonates of alkali metals and alkaline earth metals, and in addition alkali metal alcoholates, for example potassium tert-butylate and sodium methylate. As hydrophilic agent it is possible to use e.g. dicyclohexylcarbodiimide. Processes 1 and 2 are carried out at a reaction temperature between −10° and 120° C., usually between 20° and 80° C., under normal or elevated pressure and preferably in an inert solvent or diluent. Examples of suitable solvents or diluents are: ether and ethereal compounds, for example diethyl ether, dipropyl ether, dioxane, dimethoxyethane and tetrahydrofurane; amides, such as N,N-dialkylated carboxamides; aliphatic, aromatic and halogenated hydrocarbons, especially benzene, toluene, xylene, chloroform and chlorobenzene; nitriles, such as acetonitrile; dimethyl sulfoxide; and ketones, such as acetone and methyl ethyl ketone.

The starting materials of the formulae II and IV are known or they can be obtained by methods analogous to known ones. The compounds of the formula III are novel. They are obtained by methods similar to that described in Example 1A.

The compounds of the formula I exist in the form of a mixture of different optically active isomers if inhomogeneous optically active starting materials are used in the reaction. The different mixtures of isomers can be separated into the individual isomers by known methods. A compound of the formula I will be understood to comprise both the individual isomers and the mixtures thereof.

The compounds of the formula I are suitable for controlling a variety of pests of animals and plants. In particular, the compounds of the formula I are suitable for controlling insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

In particular, the compounds of the formula I are suitable for controlling plant-destructive insects, especially plant-destructive feeding insects, in ornamentals and crops of useful plants, especially in cotton and rice plantations (e.g. *Spodoptera littoralis, Heliothis virescens, Chilo suppressalis* and Laodelphax) and in crops of vegetables and fruit (for example *Leptinotarsa decemlineata, Myzus persicae, Laspeyresia pomonella* and *Adoxophyes reticulana*).

The compounds of the formula I are also very effective against flies, for example *Musca domestica* and mosquito larvae.

The acaricidal and/or insecticidal action can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, and chlorinated hydrocarbons.

Compounds of the formula I are also combined with particular advantage with substances which exert a synergistic or potentiating effect on pyrethroids. Examples of such compounds include: piperonyl butoxide, propynyl ethers, propynyl oximes, propynyl carbamates and propynyl phosphates, 2-(3,4-methylenedioxyphenoxy)-3,6,9-trioxaundecane (Sexamex or Sesoxane), S,S,S-tributylphosphorotrithioate, 1,2-methylenedioxy-4-(2-(octylsulfinyl)-propyl)-benzene.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyoxyethylene adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual," MC Publishing Corp., Ringwood, N.J., 1979.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

Formulation Examples

Formulation Examples for liquid active ingredients of the formula I
(throughout, percentages are by weight)

| (1) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (2) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N-methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| (3) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (4) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.
Formulation examples for solid active ingredients of the formula I
(throughout, percentages are by weight)

| (5) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalenesulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (6) Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (7) Dusts | (a) | (b) |
|---|---|---|
| active ingredient | 5% | 8% |
| talcum | 95% | — |
| kaolin | — | 92% |

Dusts which are ready for use are obtained by mixing the active ingredient with the carriers, and grinding the mixture in a suitable mill.

| (8) Extruder granulate | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (9) Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (10) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 1

(A) Preparation of α-allenyl-3-phenoxybenzyl alcohol 10 g of α-ethynyl-3-phenoxybenzyl alcohol, 2.1 g of paraformaldehyde, 5.3 g of diisopropylamine, 0.215 g of CuBr and 50 ml of dioxane are refluxed for 2 hours. The reaction mixture is cooled to 20° C., poured into a solution of 2 N HCl and extracted with ether. The organic phase is washed with 10% potassium carbonate and saturated sodium chloride solution, dried over magnesium sulfate and concentrated. The residue is chromatographed over silica gel with a 7:3 mixture of hexane/ether as eluant, affording the compound of the formula

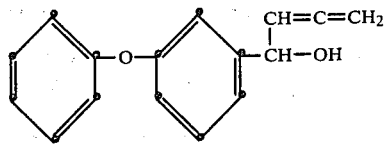

with a refractive index of $n_D^{20°} = 1.5942$.

The following compounds are prepared in analogous manner:

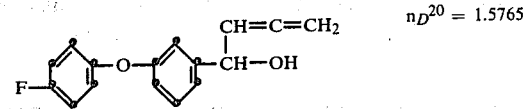 $n_D^{20} = 1.5765$

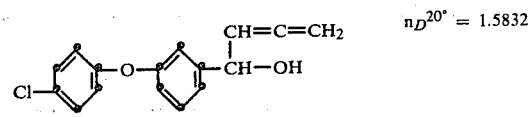 $n_D^{20°} = 1.5832$

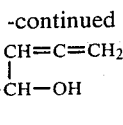 $n_D^{20°} = 1.5893$ (B) Preparation of α-allenyl-3-phenoxybenzyl-2,2-dimethyl-3-(2,2-dichlorovinyl)cyclopropane-1-carboxylate A solution of 5 g of α-allenyl-3-phenoxybenzyl alcohol in 20 ml of toluene is added dropwise at 0° C. to a mixture of 4.8 g of 2,2-dimethyl-3-(2,2-dichlorovinyl)-cyclopropanecarboxylic acid chloride, 2.2 ml of pyridine and 20 ml of toluene. The reaction mixture is stirred for 18 hours at 20° C., poured into 2 N hydrochloric acid and extracted with toluene. The organic phase is washed with 10% potassium carbonate and saturated sodium chloride solution, dried over magnesium sulfate and concentrated. The crude product is chromatographed over silica gel with a 1:10 mixture of ether/hexane as eluant, affording the compound of the formula

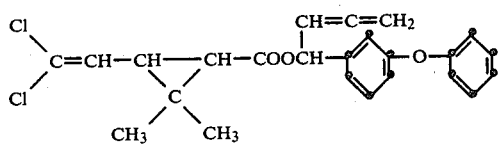

with a refractive index of $n_D^{20°} = 1.5757$.

The following compounds are prepared in analogous manner:

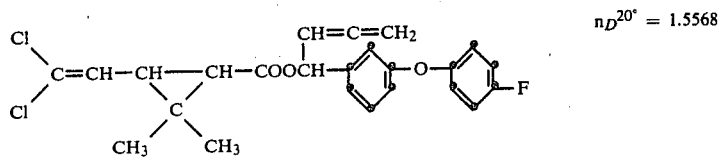 $n_D^{20°} = 1.5568$

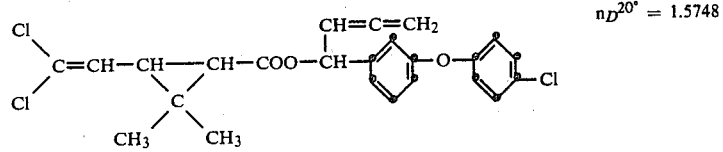 $n_D^{20°} = 1.5748$

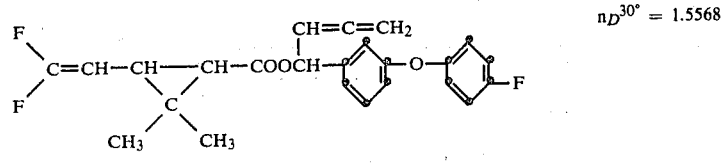 $n_D^{30°} = 1.5568$

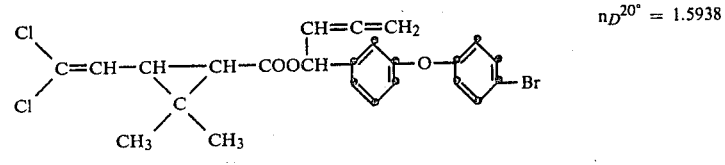 $n_D^{20°} = 1.5938$

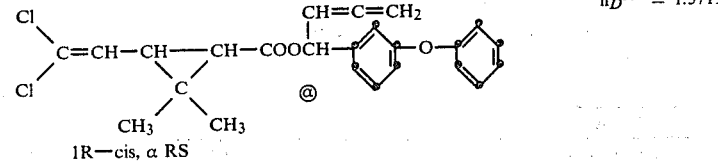 $n_D^{35°} = 1.5719$

1R—cis, α RS

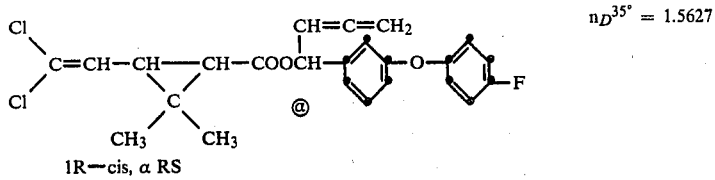

$n_D^{35°} = 1.5627$

1R—cis, α RS

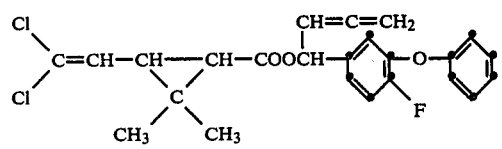

BIOLOGICAL EXAMPLES

Example 2

Insecticidal stomach poison action against *Spodoptera littoralis* and *Heliothis virescens*

Cotton plants are sprayed with a solution containing 50, 100, 200 or 400 ppm of the compound to be tested. After the coating has dried, the plants are populated with larvae of the species *Spodoptera littoralis* (L3-stage) or *Heliothis virescens* (L3-stage). Two plants are used for each test compound and test species. A mortality count is made after 2, 4, 24 and 48 hours. The test is carried out at 28° C. and 60% relative humidity.

Within the above concentration limits, the compounds of Example 1 are effective against larvae of the species *Spodoptera littoralis* and *Heliothis virescens* (vide Table).

EXAMPLE 3

Acaricidal action

Twelve hours before the test for acaricidal action, *Phaseolus vulgaris* plants are infected with an infested piece of leaf from a mass culture of *Tetranychus urticae*. The mobile stages which have migrated to the plants are sprayed from a chromatography atomiser with a solution containing 50, 100, 200, 400 and 800 ppm of the compound to be tested, such that the spray mixture does not run off. A count of living and dead organisms is made under a stereoscopic microscope after 7 days and expressed in percentage values. During the test run the plants are stood in greenhouse compartments at 25° C.

Within the above concentration limits, the compounds of Example 1 are effective against adults, larvae and eggs of *Tetranychus urticae* (vide Table).

EXAMPLE 4

Feeding and depth action against *Adoxophyes reticulana* (L3 larvae)

Two small apple trees (20 cm high) are each infected with 5 to 8 L3 larvae of *Adoxophyes reticulana*. Over 3 days these larvae are afforded the opportunity to roll themselves up into a leaf. Before the treatment, the leaves are first examined for rolled up larvae. Any larvae not or insufficiently rolled up are removed. Three days after infestation each of the apple trees is sprayed with 25 ml of a solution containing 50 or 100 ppm of the compound to be tested. A count of living and dead larvae is made 3 days after the treatment. Within the above indicated concentration limits, compounds according to Example 1 are effective against L3 larvae of *Adoxophes reticulana* (vide Table).

Biological test results

Test results based on the preceding Examples are reported in the following table, using the following rating to indicate the percentage kill of the pests:

A: 70-100% kill at a concentration of 50 ppm
B: 70-100% kill at a concentration of 100 ppm
C: 70-100% kill at a concentration of 200 ppm
D 70-100% kill in a concentration of 400 ppm

TABLE

Compounds $$\begin{array}{c} X_1 \\ \phantom{X}\diagdown \\ \phantom{XXX}C=CH-CH-CH-COOCH-\text{(Ar)}-O-\text{(Ar)} \\ X_1 \diagup \phantom{XXXXX} \diagdown C \diagup \phantom{XXXXXX} | \phantom{XX} Y_1 \phantom{XXX} Y_2 \\ \phantom{XXXXX} CH_3 \phantom{X} CH_3 \phantom{XXX} CH=C=CH_2 \end{array}$$

|     |     |      | Activity | | | |
| --- | --- | --- | --- | --- | --- | --- |
| $X_1$ | $Y_1$ | $Y_2$ | *Spodoptera littoralis* larvae | *Heliothis virescens* larvae | *Tetranychus urticae* larvae | *Adoxophyes reticulana* larvae |
| Cl | H | H | A | B | B | A |
| Cl | H | 4-F | B | B | B | B |
| Cl | H | 4-Cl | B | B | C | B |
| F | H | 4-F | C | D | D | A |

What is claimed is:

1. A cyclopropanecarboxylic acid α-allenyl-3-phenoxybenzyl ester of the formula

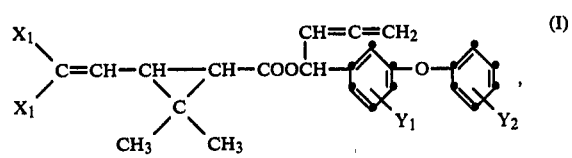

(I)

wherein $X_1$ is halogen and each of $Y_1$ and $Y_2$ is hydrogen or halogen.

2. A compound according to claim 1, wherein $X_1$ is fluorine or chlorine, $Y_1$ is hydrogen and $Y_2$ is hydrogen, fluorine, chlorine or bromine.

3. A compound according to claim 2, wherein $X_1$ is chlorine, and $Y_2$ is hydrogen, fluorine or chlorine.

4. The compound according to claim 3 of the formula

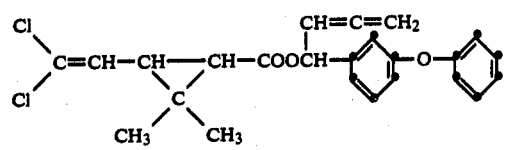

5. The compound according to claim 3 of the formula

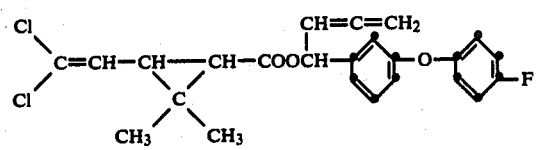

6. The compound according to claim 3 of the formula

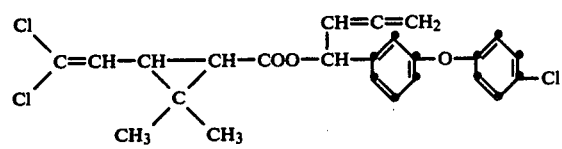

7. A compound according to claim 2 of the formula

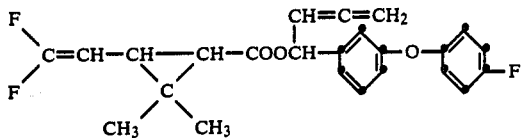

8. A compound according to claim 2 of the formula

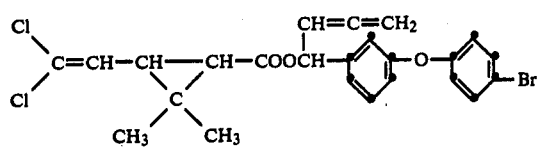

9. The compound according to claim 4 having the optical configuration of (1R, cis) in the acid moiety and (RS) in the alcohol moiety.

10. The compound according to claim 5 having the optical configuration of (1R, cis) in the acid moiety and (RS) in the alcohol moiety.

11. A method of controlling insects and acarids at a locus, which method comprises applying to said locus an insecticidally or acaricidally effective amount of a cyclopropanecarboxylic acid α-allenyl-3-phenoxybenzyl ester of the formula

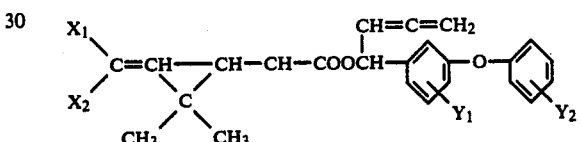

wherein $X_1$ is halogen and each of $Y_1$ and $Y_2$ is hydrogen or halogen.

12. A insecticidal and acaricidal composition which comprises an insecticidally or acaricidally effective amount of a cyclopropanecarboxylic acid α-allenyl-3-phenoxybenzyl ester of the formula

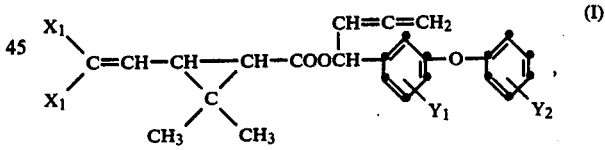

(I)

wherein $X_1$ is halogen and each of $Y_1$ and $Y_2$ is hydrogen or halogen together with a suitable carrier.

* * * * *